(12) United States Patent
Liwa

(10) Patent No.: US 9,250,667 B2
(45) Date of Patent: Feb. 2, 2016

(54) EARLY DETECTION OF OVERHEATING DEVICES

(71) Applicant: International Business Machines Corporation, Armonk, NY (US)

(72) Inventor: Francisco D Liwa, Singapore (SG)

(73) Assignee: International Business Machines Corporation, Armonk, NY (US)

( * ) Notice: Subject to any disclaimer, the term of this patent is extended or adjusted under 35 U.S.C. 154(b) by 254 days.

(21) Appl. No.: 14/042,967

(22) Filed: Oct. 1, 2013

(65) Prior Publication Data

US 2014/0032944 A1    Jan. 30, 2014

Related U.S. Application Data

(63) Continuation of application No. 13/448,051, filed on Apr. 16, 2012, now Pat. No. 8,910,508.

(51) Int. Cl.
*G06F 1/20*     (2006.01)
*G01N 33/00*    (2006.01)

(52) U.S. Cl.
CPC ............ *G06F 1/206* (2013.01); *G01N 33/0004* (2013.01); *G01N 33/0034* (2013.01)

(58) Field of Classification Search
CPC ................................ G01N 33/00; G06F 1/206
USPC ........................................................ 73/23.34
See application file for complete search history.

(56) References Cited

U.S. PATENT DOCUMENTS

| | | | |
|---|---|---|---|
| 5,115,225 A | 5/1992 | Dao et al. | |
| 5,623,212 A * | 4/1997 | Yamanaka | G01N 27/122 324/693 |
| 6,085,576 A * | 7/2000 | Sunshine | G01N 33/0031 340/634 |
| 6,411,905 B1 | 6/2002 | Guoliang et al. | |
| 7,936,147 B2 * | 5/2011 | Kook | H02J 7/0044 320/108 |
| 8,052,932 B2 | 11/2011 | Han et al. | |

(Continued)

FOREIGN PATENT DOCUMENTS

| | | |
|---|---|---|
| JP | 04186139 | 7/1992 |
| JP | 04186139 A * | 7/1992 |

OTHER PUBLICATIONS

Yamashita, Takayuki et al. "Overheat Sensing System using an Odor Detector and Capsules 'CAN-NETSU-KUN'". Hitachi Cable Review No. 22. Aug. 2003.*

(Continued)

*Primary Examiner* — Hezron E Williams
*Assistant Examiner* — Mark A Shabman
(74) *Attorney, Agent, or Firm* — Kunzler Law Group; Damion Josephs

(57) ABSTRACT

A method is provided that monitors the odor within the physical enclosure of a computing device that includes one or more components. The method includes determining whether the odor within the physical enclosure is indicative of an overheating component that is overheating within the physical enclosure of the computing device. Determining whether the odor within the physical enclosure may include an artificial neural network ("ANN") to determine whether the odor is indicative of an overheating component. The method includes initiating an overheating protocol in response to determining that the odor within the physical enclosure is indicative of an overheating component. The method may, for example, alert the user and/or applications that a component is overheating.

7 Claims, 9 Drawing Sheets

(56) References Cited

U.S. PATENT DOCUMENTS

| | | | |
|---|---|---|---|
| 2002/0000115 A1* | 1/2002 | Nakano | G01N 33/0047 73/23.34 |
| 2006/0191319 A1 | 8/2006 | Kurup | |
| 2008/0150556 A1* | 6/2008 | Han | B82Y 15/00 324/693 |
| 2010/0035355 A1 | 2/2010 | Buki et al. | |
| 2011/0209524 A1 | 9/2011 | Ziglioli et al. | |
| 2011/0212349 A1 | 9/2011 | Naruse et al. | |

OTHER PUBLICATIONS

Ymashita, Takayuki et al, "Overheat System using an odor Capsules" CAN-NETSU-KUM, Hitachi Cable Review, No. 22, Aug. 2003.

U.S. Appl. No. 13/448,051, Office Action, Mar. 18, 2014.

Arshak, K., et al, "A review of gas sensors employed in electronic nose applications." Research Article, Sensor Review, vol. 24, No. 2-2004, pp. 181-198. Emerald Group Publishing Limited. 2004.

Kang, I., et al, "Introduction to carbon nanotube and nanofiber smart materials," Research Article, Science Direct, Composite: Part B 37 (2006) 382-394. 2006.

Lampety, L., et al, "Magnetoresistance of electrospun carbon nanofibers pyrolyzed at low temperatures," Research Article, University of Pennsylvania—Center for Sensor Technologies, Technical Report TR17OCT03 pp. 182-196. 2003.

Patel, H., et al, "Nose on a chip," Research Article, Merit Bien, 2011.

Stetter, J., et al, "Sensors: Engineering Structures and Materials from Micro to Nano," Article, The Electrochemical Society Interface. Spring 2006.

U.S. Appl. No. 13/448,051, Notice of Allowance, Mailed Jul. 8, 2014.

* cited by examiner

EARLY DETECTION OF OVERHEATING DEVICES

CROSS-REFERENCE TO RELATED APPLICATIONS

This application is a continuation of U.S. patent application Ser. No. 13/448,051 entitled "EARLY DETECTION OF OVERHEATING DEVICES" filed on Apr. 16, 2012 for Francisco D. Liwa, the entire contents of the above mentioned application is incorporated herein by reference for all purposes.

FIELD

The subject matter disclosed herein relates to an approach to detecting overheating devices, and particularly to detecting overheating components of computing devices using odor sensors.

BACKGROUND

Description of the Related Art

Computing devices (such as laptops, cell phones, tablets, desktops, servers, and others) generally include a number of components that allow the computing device to operate. For example, a computing device may have a central processing unit (CPU), a graphics processing unit (GPU), memory devices, and others. A failure of one or more of these components may cause a failure of the computing device itself. Components in a computing device often fail because they overheat.

In order to prevent overheating, computing devices often include internal sensors (such as temperature sensors) that monitor the internal temperature of the computing device. If the internal temperature gets too high, the computing device may be shut down to prevent further damage. However, temperature sensors are not always sufficiently accurate; if a sensor is located too far away from a component, that component may overheat and fail before it raises the internal temperature sufficiently to cause the temperature sensor to shut down the computing device. Even if an overheating component is not destroyed when it overheats, the overheating component may be damaged, and the stability of the computing device may be negatively impacted.

BRIEF SUMMARY

One embodiment of an apparatus includes a sensor module that monitors an odor within a physical enclosure of a computing device, the physical enclosure comprising one or more components. The apparatus may also include a recognition module that determines that the odor within the physical enclosure is indicative of an overheating component that is overheating within the physical enclosure of the computing device. The apparatus may further include an alert module that initiates an overheating protocol in response to determining that the odor within the physical enclosure is indicative of the overheating component.

In another embodiment, the invention may be realized as a method. The method may involve monitoring an odor within a physical enclosure of a computing device comprising one or more components, determining that the odor within the physical enclosure is indicative of an overheating component that is overheating within the physical enclosure of the computing device, and initiating an overheating protocol in response to determining that the odor within the physical enclosure is indicative of the overheating component.

The invention may, in certain embodiments, be realized as a system. The system may include a computing device that comprises a physical enclosure, one or more components situated within the physical enclosure, and a sensing material situated within the physical enclosure. The sensing material may be reversibly altered by odor molecules.

The system may also involve an odor apparatus. The odor apparatus may include a sensor module that monitors an odor within the physical enclosure. The odor apparatus may also include a recognition module that determines that the odor within the physical enclosure is indicative of an overheating component that is overheating within the physical enclosure of the computing device. The odor apparatus may also include an alert module that initiates an overheating protocol in response to determining that the odor within the physical enclosure is indicative of the overheating component.

In one embodiment, a computing device is provided with a physical enclosure, one or more components situated within the physical enclosure, and an odor apparatus. The odor apparatus may include a sensor module that monitors the odor within the physical enclosure of the computing device. The sensor module may comprise a sensing material for detecting the odor. The electrical properties of the sensing material may be altered by odor molecules of the odor, which alteration in the electrical properties of the sensing material can be detected and quantified by the sensor module.

The odor apparatus may also include a recognition module that determines that the odor within the physical enclosure is indicative of an overheating component that is overheating within the physical enclosure of the computing device. The recognition module may comprise an artificial neural network that compares the alteration in the sensing material with a reference database comprising a plurality of reference alterations caused by the overheating component. The odor apparatus may also include an alert module that initiates an overheating protocol in response to determining that the odor within the physical enclosure is indicative of the overheating component.

Other embodiments of the invention may also be realized, and the foregoing summary is provided for convenience, and not by way of limitation.

BRIEF DESCRIPTION OF THE DRAWINGS

In order that the advantages of the embodiments of the invention will be readily understood, a more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which:

FIG. 2, which includes

FIG. 7, which includes

DETAILED DESCRIPTION OF THE INVENTION

Figure 1:
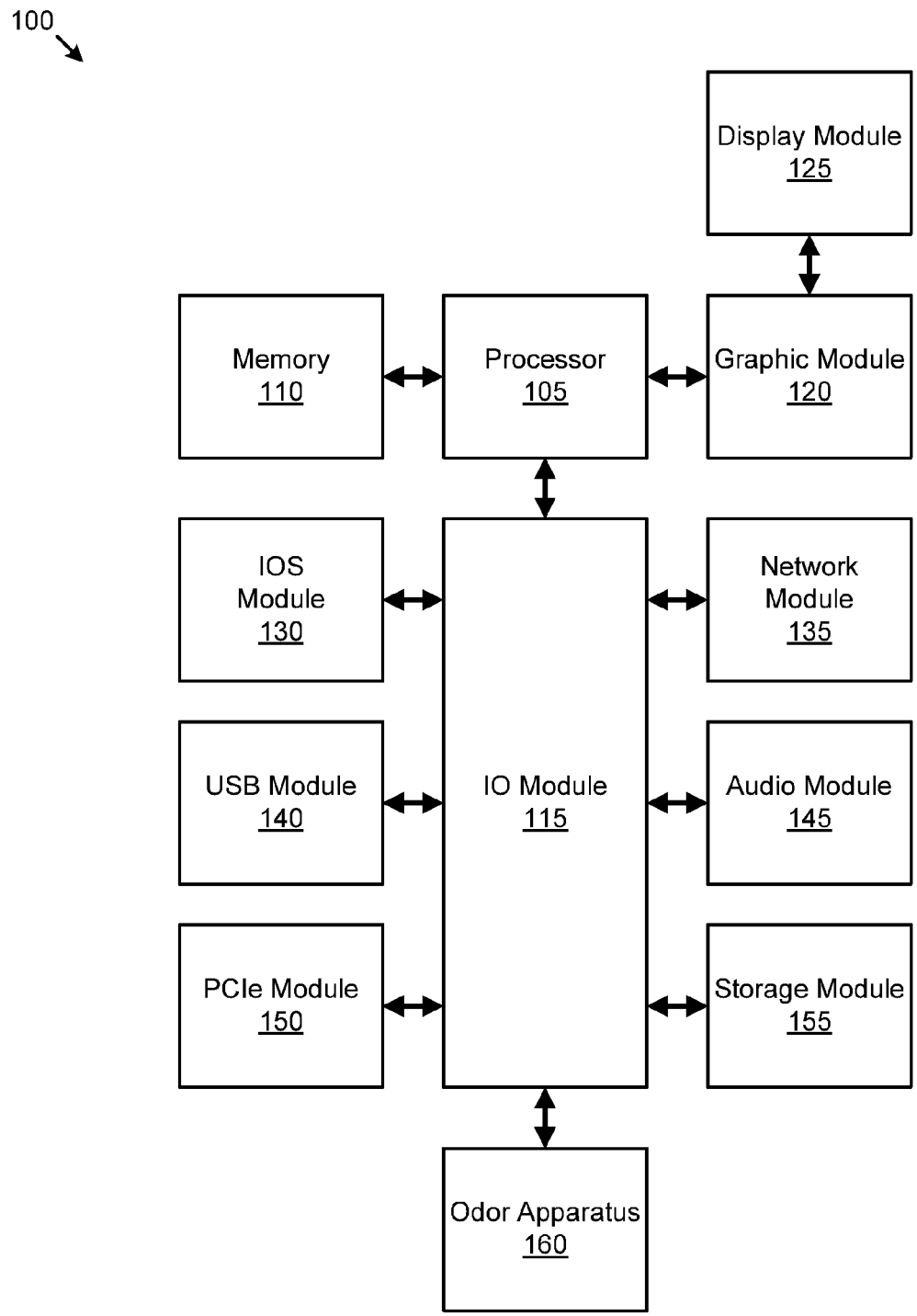
FIG. 1 is a schematic block diagram illustrating one embodiment of a computing system comprising an odor apparatus.

References throughout this specification to features, advantages, or similar language do not imply that all of the features and advantages may be realized in any single embodiment. Rather, language referring to the features and advantages is understood to mean that a specific feature, advantage, or characteristic is included in at least one embodiment. Thus, discussion of the features and advantages, and similar language, throughout this specification may, but do not necessarily, refer to the same embodiment.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims, or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireline, optical fiber, Radio Frequency (RF), or the like, or any suitable combination of the foregoing In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++, PHP or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by computer readable program code. The computer readable program code may be provided to a processor of a general purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The computer readable program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The computer readable program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and computer readable program code.

FIG. 1 is a schematic block diagram illustrating one embodiment of a computing device 100. The computing device 100 shown in FIG. 1 includes a processor 105, a memory 110, an IO module 115, a graphic module 120, a display module 125, an input/output system ("IOS") module 130, a network module 135, a universal serial bus ("USB") module 140, an audio module 145, a peripheral component interconnect express ("PCIe") module 150, a storage module 155, and an odor apparatus 160. One of skill in the art will recognize that other configurations of a computing device 100 may be employed with the embodiments described herein.

The processor 105, memory 110, IO module 115, graphic module 120, display module 125, IOS module 130, network module 135, USB module 140, audio module 145, PCIe module 150, storage module 155, and/or thermal odor apparatus 160 are examples of components in a computing device 100. A component, as that term is used in this application, refers to a physical device in a computing device 100 that performs one or more functions. These components (and others not shown) may be fabricated using semiconductor gates on one or more semiconductor substrates. Each semiconductor substrate may be packaged in one or more semiconductor devices mounted on circuit cards. Connections between the components may be through semiconductor metal layers, substrate-to-substrate wiring, circuit card traces, and/or wires connecting the semiconductor devices. In some embodiments, a computing device 100 may only include a subset of the components 105-160 shown in FIG. 1.

The memory 110 stores computer readable programs. The processor 105 executes the computer readable programs. The computer readable programs may be tangibly stored in the storage module 155. The storage module 155 may be a solid state device ("SSD"). The storage module 155 may be a hard disk drive, an optical storage device, a holographic storage device, a micromechanical storage device, or the like.

The processor 105 may include integrated cache to reduce the average time to IO Module 15. The integrated cache may store copies of instructions and data from the most frequently used memory 110 locations. The processor 105 may communicate with the memory 110 and the graphic module 120.

In addition, the processor 105 may communicate with the IO module 115. The IO module 115 may support and communicate with the IOS module 130, the network module 135, the PCIe module 150, the storage module 155, and/or the camera module 106.

The PCIe module 150 may communicate with the IO module 115 for transferring/receiving data or powering peripheral devices. The PCIe module 150 may include a PCIe bus for attaching the peripheral devices. The PCIe bus can logically connect several peripheral devices over the same set of connections. The peripherals may be selected from a printer, a joystick, a scanner, a camera, or the like. The PCI module 150 may also comprise an expansion card as is well known to those skilled in the art.

The IOS module 130 may communicate instructions through the IO module 115 to boot the computing device 100, so that computer readable software instructions stored on the storage module 155 can load, execute, and assume control of the computing device 100. Alternatively, the IOS module 130 may comprise a coded program embedded on a chipset that recognizes and controls various devices that make up the computing device 100.

The IOS module 130 refers to various approaches to providing a firmware interface for booting an computing device 00, including traditional basic input output system ("BIOS"), unified extensible firmware interface (UEFI), Open Firmware, and others. The IOS module 130 may be a solid state storage device with relevant code that is attached to a motherboard of the computing device 100.

The network module 135 may communicate with the IO module 115 to allow the computing device 100 to communicate with other devices over a network. The devices may include routers, bridges, computers, information processing systems, printers, and the like. The display module 125 may communicate with the graphic module 120 to display information. The display module 125 may include a cathode ray tube ("CRT"), a liquid crystal display ("LCD") monitor, or the like. The USB module 140 may communicate with one or more USB compatible devices over a USB bus. The audio module 145 may generate an audio output.

Components of the computing device 100 generally require power to operate, and create heat as a result. The computing device 100 may include fans and other cooling components that regulate the temperature of the computing device 100. The computing device 100 may also include temperature sensors that measure the temperature within the computing device 100. The temperature sensors may monitor the internal temperatures of the computing device 100. This information may be used to control the speed at which fans within the computing device 100 run. The temperature sensors may also be used to monitor for overheating components within the computing device 100.

The computing device 100 may also include an odor apparatus 160. As explained above, temperature sensors may not be able to adequately detect overheating components; for example, if a temperature sensor is not close to the graphic module 120, and the graphic module 120 is overheating, the graphic module 120 may be damaged before the temperature sensor registers the high temperature. The odor apparatus 160 monitors the odor within the physical enclosure of the computing device 100, and determines whether or not the odor is indicative of an overheating component that is overheating within the physical enclosure of the computing device 100. The odor apparatus 160 may initiate an overheating protocol in response to determining that the odor within the physical enclosure is indicative of an overheating component.

Those of skill in the art will appreciate that FIG. 1 shows only one possible configuration of components within a computing device 100. Depending on the nature and needs of the computing device 100, the computing device 100 may include more or fewer components than those shown. Similarly, the components may be arranged in a configuration other than that shown in FIG. 1.

Figure 2A:
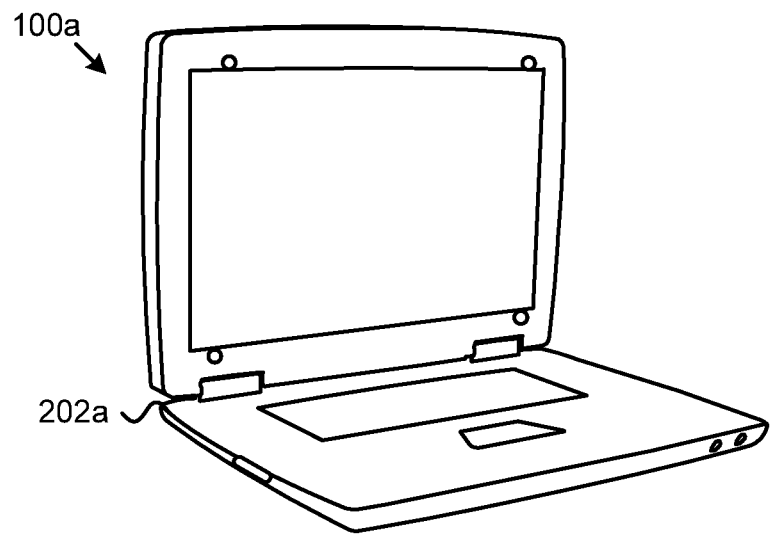
FIGS. 2A and 2B, is an illustration of two example computing systems having physical enclosures that may incorporate an odor apparatus.
Figure 2B:
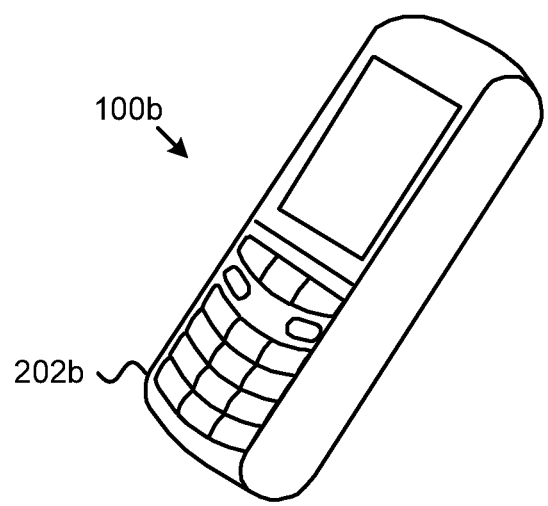

FIG. 2 shows two separate, example embodiments of a computing device 100. FIG. 2a shows a computing device 100a that is a laptop computer. FIG. 2b shows a computing device 100b that is a cellular phone. The computing device 100 may also be, in certain embodiments, a tablet computer, a cellular phone, a desktop computer, or a server. Other implementations may also be used.

FIGS. 2a and 2b also show the physical enclosures 202 of the computing devices 100. The physical enclosure 202 refers to the physical form factor that provides protection for components of the computing device 100. For example, the physical enclosure 202a of the computing device 100a may contain a motherboard, hard disk drives, and various components. Similarly, the physical enclosure 202b of the computing device 100b may contain a processor, memory, and various other components. The shape and nature of the physical enclosure 202 may vary based on the implementation; for example, a desktop computer usually has a large, rectangular shaped physical enclosure (often referred to as the chassis) with holes and fans to provide ventilation.

Figure 3:
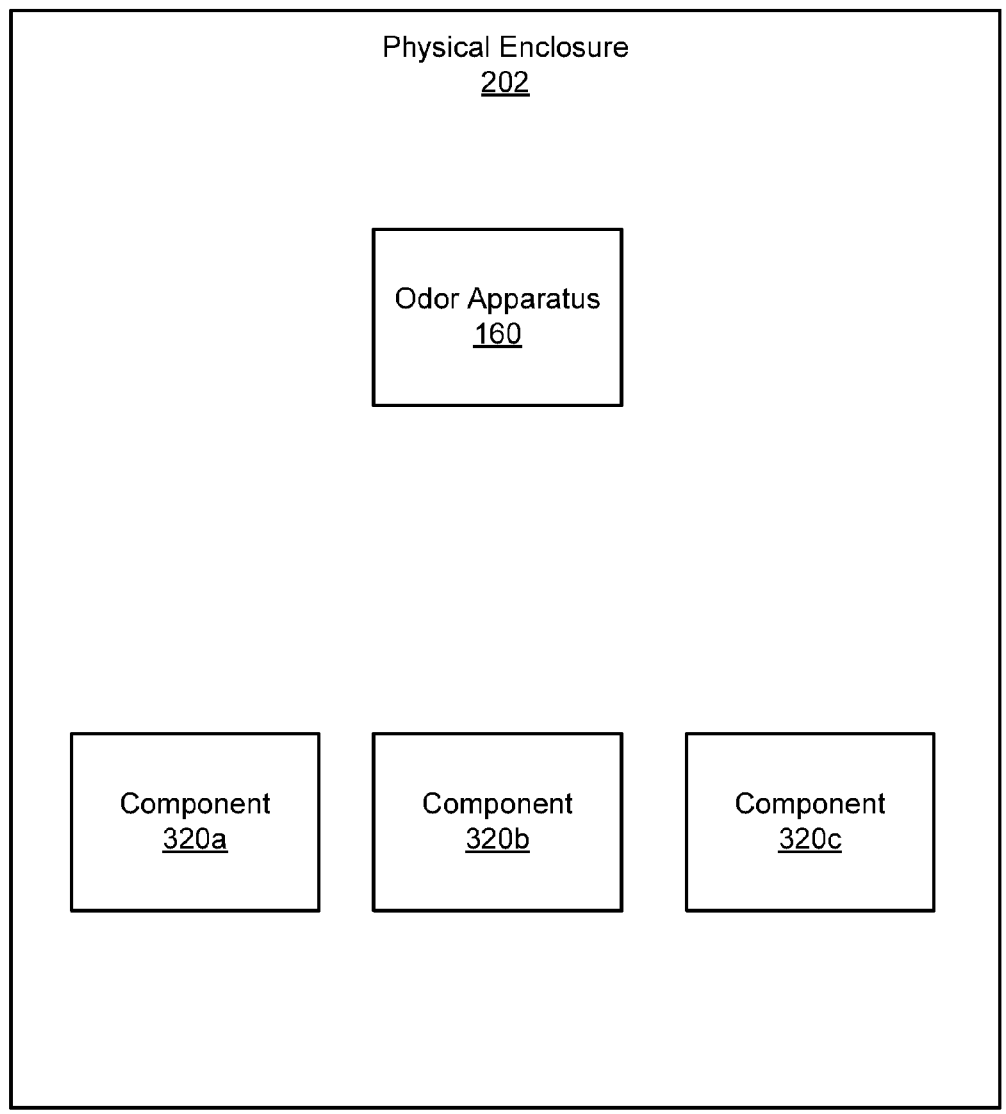
FIG. 3 is a schematic block diagram illustrating one embodiment of computing device including an odor apparatus.

FIG. 3 shows a schematic block diagram illustrating one embodiment of a computing device 100. FIG. 3 illustrates the physical enclosure 202 and, within the physical enclosure 202, the odor apparatus 160 and components 320a-c. The odor apparatus 160 may include modules, as described in greater detail below, for performing one or more functions described herein.

The odor apparatus 160 may monitor the odor within the physical enclosure 202. As used here, "odor" refers to the property of a substance (such as the air within the physical enclosure 202) that activates the sense of smell. The term "odor" is not used to convey any quality of the odor; for example, that the odor is agreeable or disagreeable. The odor apparatus 160 may detect odor molecules within the physical enclosure 202 that are indicative of an overheating component 320.

For example, an overheating graphic module 120 may emit odor molecules that register as a burning odor when smelled by a human. The odor apparatus 160 may detect and recognize the burning odor, and initiate an overheating protocol to prevent damage to the computing device 100 or further damage to the overheating component 320. The odor apparatus 160 may detect the overheating graphic module 120 before the overheating graphic module 120 raises the temperature of the physical enclosure 202 sufficiently to register with thermal sensors.

Figure 4:
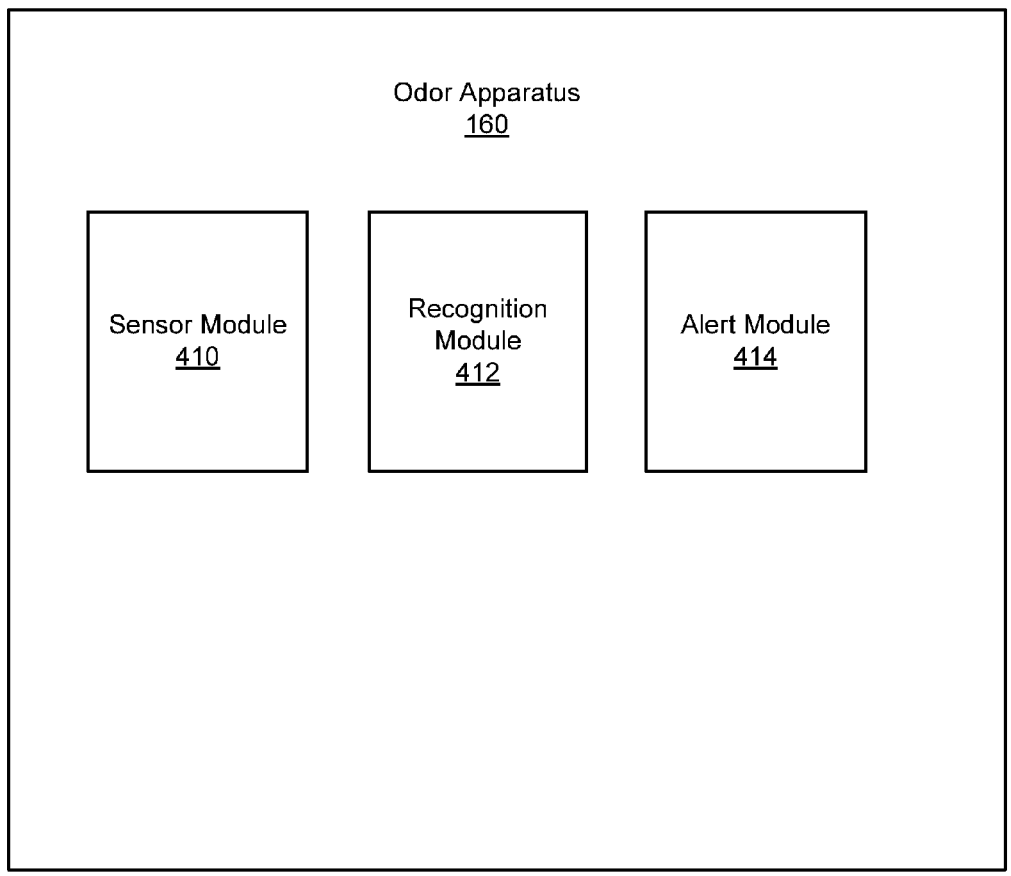
FIG. 4 is a schematic block diagram illustrating one embodiment of an odor apparatus.

FIG. 4 shows one embodiment of an odor apparatus 160. In the depicted embodiment, the odor apparatus 160 includes a sensor module 410, a recognition module 412, and an alert module 414. The odor apparatus 160 may include different modules in various implementations.

In one embodiment, the sensor module 410 monitors the odor within the physical enclosure 202 of the computing device 100. In another embodiment, the recognition module 412 determines that the odor within the physical enclosure 202 is indicative of an overheating component 320 that is overheating within the physical enclosure 202 of the computing device 100. The alert module 414, in one embodiment, initiates an overheating protocol in response to the recognition module 412 determining that the odor within the physical enclosure 202 is indicative of an overheating component 320.

As used herein, an overheating protocol refers to one or more actions that are taken in response to a component 320 of the computing device 100 overheating. The overheating protocol may specify particular actions, and a particular order for the actions. In one embodiment, the overheating protocol may comprise alerting the user that at least one component 320 within the physical enclosure 202 is overheating. In one embodiment, the overheating protocol is implemented wholly or in part by one or more of the sensor module 410, the recognition module 412, and the alert module 414.

The overheating protocol may also comprise alerting one or more applications that at least one component 320 within the physical enclosure 202 is overheating. In one embodiment, the alert module 414 implements a driver that uses the common information model (CIM) to inform applications of the detection of overheating components 320 CIM is an open standard defining how managed elements in an environment are represented, and allows consistent management of such elements. CIM allows applications and devices to exchange information about the components 320 and may also provide means to control and manage components 320 In one embodiment, the alert module 414 implements the web-based enterprise management (WBEM) implementation of CIM, including protocols for discovering and accessing CIM implementations.

In one embodiment, the overheating protocol involves shutting down the computing device 100. The alert module 414 may shut down the computing device 100 to prevent damage to the computing device 100, or further damage to components 320 The overheating protocol may also involve the alert module 414 initiating one or more diagnostic tools to check the functionality of components 320 in the computing device 100. The alert module 414 may attempt to discover which component 320 is overheating, and take appropriate remedial action, such as alerting the user, attempting to solve the problem (by, for example, installing updated firmware), or taking other appropriate action. The overheating protocol may also involve restarting the computing device 100 in a safe boot mode. This may provide the user and the alert module 414 more opportunities to accurately identify and diagnose the component 320 that is overheating while reducing the possibility of further damage.

The overheating protocol may also involve the alert module 414 creating a log entry that includes data generated in connection with the overheating component 320 For example, the alert module 414 may log the conditions that caused the recognition module 412 to determine that the odor within the physical enclosure 202 is indicative of an overheating component 320. The alert module 414 may also log the actions taken in response to detecting the overheating component 320. The log may also include the time at which the conditions occurred. Other information may also be logged by the alert module 414.

Figure 5:
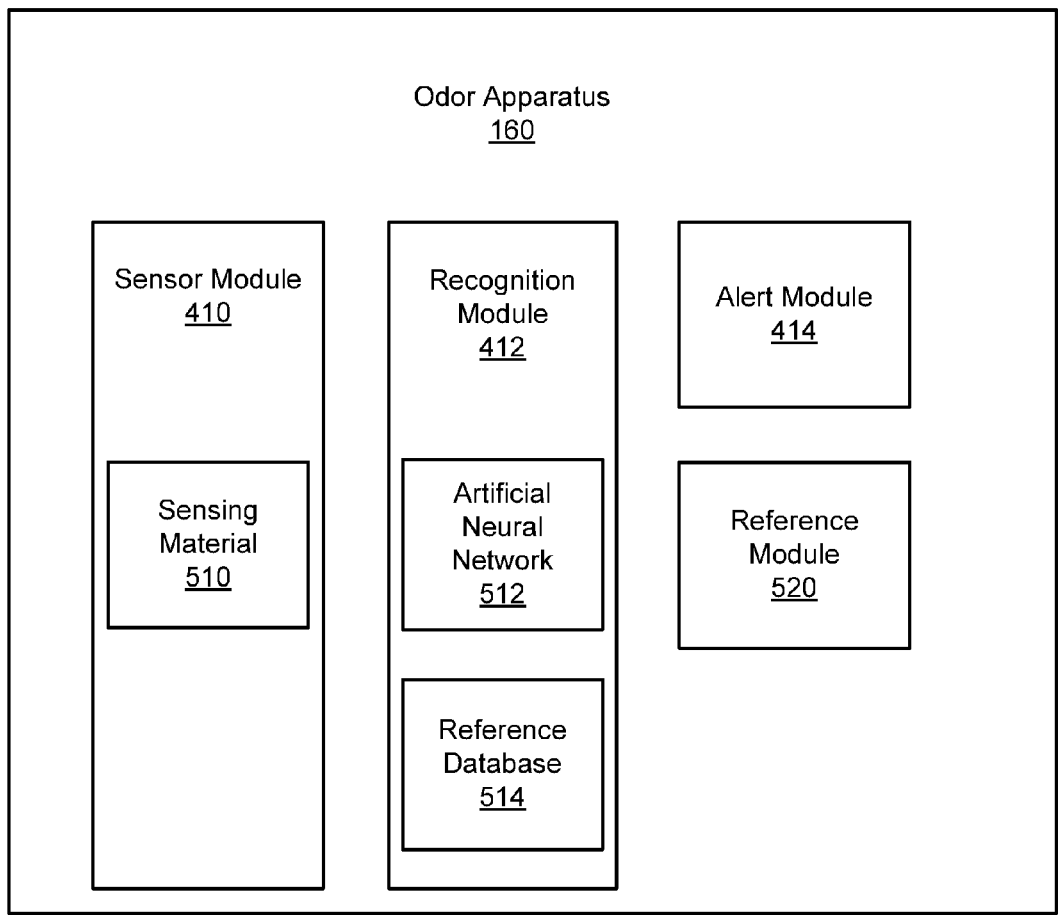
FIG. 5 is a schematic block diagram illustrating a second embodiment of an odor apparatus.

FIG. 5 shows another embodiment of the odor apparatus 160. FIG. 5 shows the sensor module 410 including sensing material 510. In one embodiment, the sensing material 510 is a material that is reversibly altered by odor molecules of the odor. In another embodiment, the sensing material 510 is irreversibly altered by the odor molecules of the odor. The sensing material 510 may be tuned to react to an odor that is indicative of an overheating component 320. When a component in the computing device 100 begins to overheat, the component 320 may emit odor molecules that register as a burning odor or other odor indicative of a component 320 being damaged. The sensing material 510 may be tuned to react to these odor molecules. The sensor module 410 may collect samples of odor molecules from within the physical enclosure 202 of the computing device 100, and put the samples in contact with the sensing material 510. For example, the sensor module 410 may use a first sample of the air within the physical enclosure 202, which will include the relevant odor molecules. The sensor module 410 may place the air sample in contact with the sensing material 510, and measure the resulting alteration in the sensing material 510. The sensor module 410 may continue to take samples in this manner at regular intervals.

In certain embodiments, the electrical properties of the sensing material 510 are altered when the sensing material 510 comes into contact with the odor molecules. The sensor module 410 may detect and quantify the alteration in the electrical properties of the sensing material 510. For example, the resistivity of the sensing material 510 may change when it is in the presence of the relevant odor molecules. In other embodiments, other characteristics of the sensing material 510 are changed when the sensing material 510 comes into contact with the odor molecules.

In one embodiment, the sensor module 410 collects the air sample, and injects the headspace into an area containing the sensing material 510. When the sensing material 510 is in contact with the odor molecules, the sensing material 510 may react in a way that reversibly alters the sensing material 510. For example, the odor molecules may change the electrical properties of the sensing material 510. The sensor module 410 may record the signal representing the change in electrical properties into a digital representation, and provide that digital representation to the recognition module 412.

In one embodiment, the sensing material 510 is a conductivity sensor. Typically, conductivity sensors work on the principle that a change in a property of the sensing material 510 that results from interacting with the odor molecules leads to a change in the resistance of the sensing material 510. Then changes in the resistance of the sensing material 510 in the presence of the odor molecules can be measured and quantified, and compared to determine whether the odor is indicative of an overheating component 320.

In another embodiment, the sensing material 510 is a metal oxide sensor that uses a change in conductance of the oxide in the sensor upon interaction with odor molecules. The metal oxide sensor may be n-type that responds to reducing gases, or p-type, which responds to oxidizing gases. The metal oxide sensor may use the metal oxide to capture the odor molecules. The quantity of the odor molecules may alter the resistance of the oxide in a measurable way, which can be used to identify the odor.

In another embodiment, the sensing material 510 is a surface acoustic wave (SAW) sensor that includes a piezoelectric substrate with an input and output inter digital transducer on top of the substrate. A membrane may be placed between the transducers, and an alternating current (AC) signal applied across the input transducer. This can create an acoustic two dimensional wave that propagates along the surface of the crystal at a depth of one wavelength at operating frequencies between 100 and 400 MHz. As odor molecules interact with the membrane, the mass of the membrane is changed, causing the frequency of the wave to alter. This alteration can be measured and used to identify the odor.

In another embodiment, the sensing material 510 is a quartz crystal microbalance (QCM) sensor that includes a piezoelectric quartz crystal. An AC voltage may be applied across the crystal, causing the crystal to oscillate at between 10 and 30 MHz. A membrane may be deposited onto the surface of the crystal. The membrane may adsorb gases when exposed to a vapor, resulting in an increase in mass. The increase in mass alters the resonant frequency of the crystal, and this change can be used to detect and identify the odor.

In another embodiment, the sensing material 510 is an optical sensor. The optical sensor may use optic fibers with a thickness of approximately 2 micrometers, and coated with a florescence dye encapsulated in a polymer matrix. The odor molecules, upon interacting with the florescence dye, may alter the polarity and consequently change the dye's optical properties. The optical changes in the florescence dye may be used to detect and identify the odor. Adsorbents, such as alumina, may be added to the polymer to improve the response by lowering the detection limits of the optical sensor.

Figure 6:
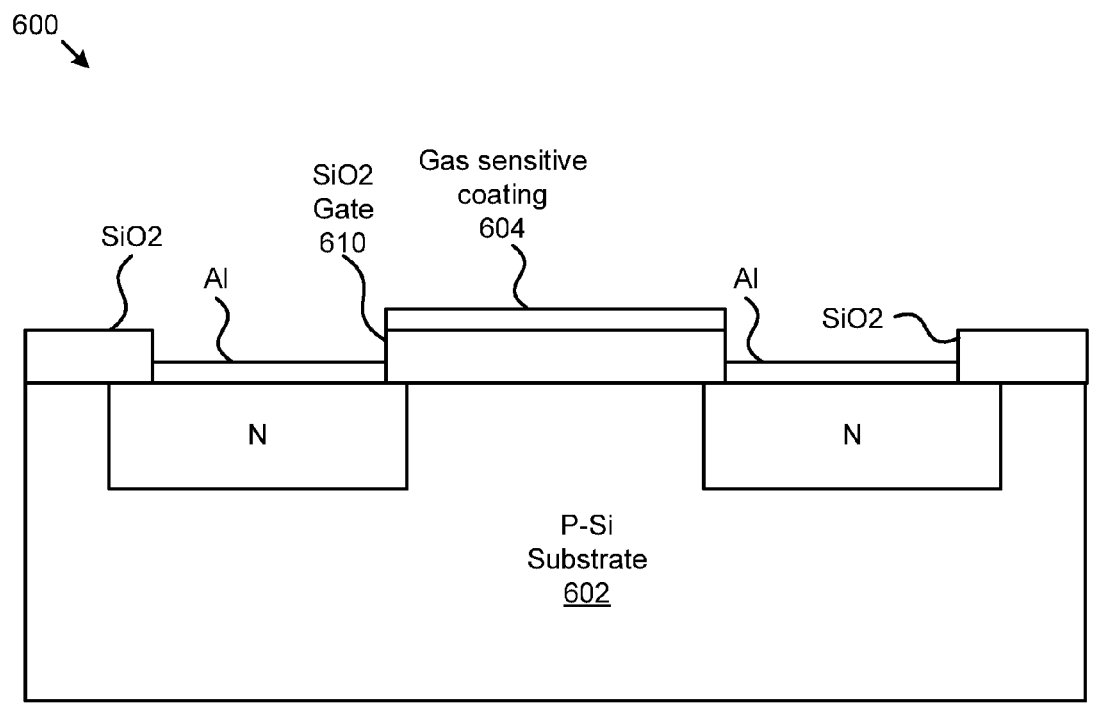
FIG. 6 is a diagram of a possible embodiment of a MOSFET used as a sensing material.

In another embodiment, the sensing material 510 is a metal oxide semiconductor field effect transistor (MOSFET) that acts as a transducer that represents the odor as an electrical signal. FIG. 6 shows one example of a MOSFET sensor 600. The MOSFET sensor 600 may be a metal-insulator-semiconductor (MIS) device. The MOSFET sensor 600 may include a P-Si substrate 602. Other materials may also be used for the substrate, depending on the implementation. The odor molecules may interact with the gate 610 material in the MOSFET and change the threshold voltage of the MOSFET due to the changes in the work functions of the metal and the oxide layers. The odor molecules may interact with the catalytically active surface, changing the work functions due to the polarization of the surface and interface of the catalytic metal and the oxide layer. A porous, gas sensitive coating 604 may be applied to the gate 610 to allow diffusion of the odor molecules, allowing the odor molecules to interact with the metal insulator interface. The odor molecules may be detected by monitoring for changes in the drain-source current and the gate 610 voltage.

In another embodiment, as odor molecules enter the area of the MOSFET sensor 600, the odor molecules will be charged either positively or negatively, affecting the electric field inside the MOSFET sensor 600. The changes in the MOSFET signal caused by the introduction of charged molecules can be measured and interpreted in order to identify the odor molecules. Other approaches using a MOSFET sensor 600 to sense odors may also be used.

Figure 7A:
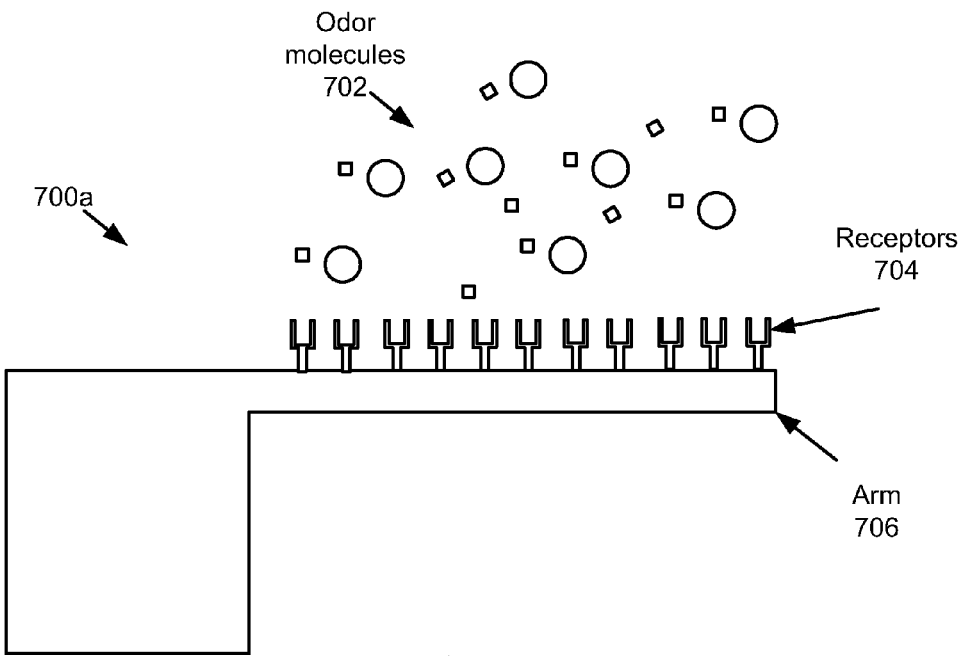
FIGS. 7A and 7B, is a diagram illustrating an embodiment of a carbon nanofiber sensing material.
Figure 7B:
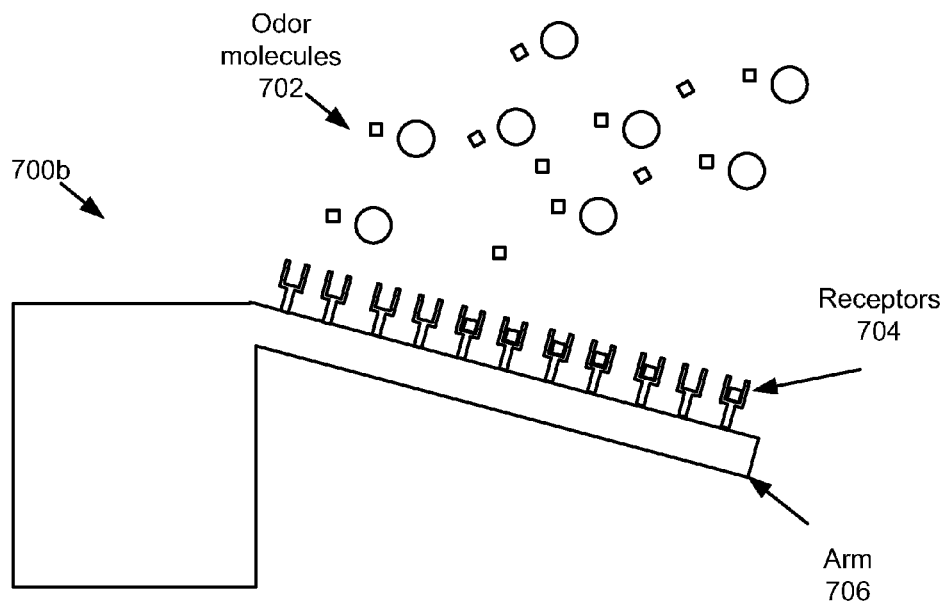

FIGS. 7A and 7B show an example of a sensing material 510 that is a carbon nano fiber (CNF) or a carbon nanotube sensor 700. The CNF sensor 700 may be solid-state transducers that have piezoelectric, pyroelectric, electrostrictive, magnetostrictive, piezoresistive, electroactive, or other sensing and actuating properties. The CNF sensor 700 may be implemented as nano materials.

The CNF sensor 700 may display a piezoresistance property, whereby the CNF sensor 700 changes its resistivity when it interacts with the relevant odor molecules (shown as 702 in FIGS. 7A and 7B). The CNF sensor 700 may have receptors 704 that are designed to interact with the relevant odor molecules 702. As shown in FIG. 7B, the odor molecules 702 may engage the receptors 704, and provide a mechanical strain on the arm 706 of the CNF sensor 700. The mechanical strain on the arm 706 may alter the band structure of the CNF sensor 700, which may increase or decrease the conductance of the CNF sensor 700 depending on the chirality of the carbon nanofiber. By altering the band structure, the quantum states available to the electrons is affected, which may thereby affect the conductance of the CNF sensor 700. These changes in the conductance of the CNF sensor 700 may be measured and quantified, and used for identifying the odor. In certain embodiments, the CNF sensor 700 removes the odor molecules 702 from the receptors 704 after the sampling is complete, thus allowing the CNF sensor 700 to test additional samples of odor as part of the determination of whether any components 320 in the computing device 100 are overheating.

The above are examples of possible sensing materials 510. Other approaches to sensing and quantifying an odor using sensing materials 510 may also be used in addition to, or instead of, the specific examples given above. In one embodiment, the odor apparatus 160 is installed as a component on the motherboard of the computing device 100, thus allowing the odor apparatus 160 to be situated within the physical enclosure 202 and to have access to the relevant odors. If there is a sufficient concentration of odor molecules 702 within the sample in contact with the sensing material 510, the sensing material 510 may be sufficiently altered to cause the recognition module 412 to determine that the odor within the physical enclosure 202 is indicative of an overheating component 320.

Returning to FIG. 5, the odor apparatus 160 may also include a recognition module 412. The recognition module 412 determines that the odor within the physical enclosure 202 is indicative of an overheating component 320. As discussed above, the sensor module 410 may make the physical characterization of the odor and create a representation of that odor. The representation may be a digital representation of the odor. The sensor module 410 may provide the digital representation of the odor to the recognition module 412.

The recognition module 412 may use threshold values to determine whether the odor within the physical enclosure 202 is indicative of an overheating component 320. For example, the recognition module 412 may be configured to determine that the odor is indicative of an overheating component 320 in response to the current in a sensor being reduced below a threshold amount. A change in the resistivity of a sensor, caused by the odor molecules 702, may cause the reduction in current. In certain embodiments, the threshold values are predetermined and set by a designer of the system. While the above example uses the example of a threshold current, other thresholds could be used and measured. Other suitable thresholds may include, for example, resistivity and voltage.

The recognition module 412 may include a reference database 514 that includes reference alterations in the sensing material 510 that were caused by an overheating component 320. The reference alterations may be one or more patterns that represent alterations that occur in response to an overheating component 320; the reference alterations may be a set of one or more rules for recognizing an alteration that is indicative of an overheating component 320. The recognition module 412 may determine that the alteration in the sensing material 510 corresponds to one or more reference alterations in the reference database 514 as part of the process of determining that the odor within the physical enclosure 202 is indicative of an overheating component 320.

The recognition module 412 may also include an artificial neural network (ANN) 512. The ANN 512 may use a connectionist approach to computation, and may consist of one or more nodes. The ANN 512 may be trained to recognize an alteration in the sensing material 510 that is indicative of an overheating component 320. The ANN 512 may be trained using the data in the reference database 514. The ANN 512 may be trained using supervised learning approaches, unsupervised learning approaches, reinforcement learning, or some combination thereof. Similarly, the ANN 512 may be trained using any of a variety of learning algorithms. The ANN 512 may, for example, use evolutionary methods, simulated annealing, expectation-maximization, non-parametric methods, particle swarm optimization, or other learning algorithms that the designer may choose to use.

The ANN 512 may be used to infer a function that predicts whether an odor is indicative of an overheating component 320 based on odor data from previous instances of overheating components 320. The ANN 512 may approach the problem of recognizing an alteration in the sensing material 510 a pattern recognition problem. The ANN 512 may learn to recognize that a particular alteration fits the pattern, and thus identify the odor as one that is indicative of an overheating component 320 within the physical enclosure 202 of the computing device 100.

The ANN 512 may be initially trained with alterations in sensing material 510 that is indicative of an overheating component 320. For example, the ANN 512 may be presented with alterations that were generated when one or more components 320 were intentionally overheated. This alteration data may be used to train the ANN 512 to recognize alterations that are indicative of components 320 that are overheating. In certain embodiments, the ANN 512 is configured to continue learning based on the alterations that occur in the sensing material 510 in the live environment. This additional learning may supplement the initial training performed using the alterations generated when components 320 where intentionally overheated.

In one embodiment, the recognition module 412 uses fuzzy logic to determine whether the odor is indicative of an overheating component 302. The recognition module 412 may use fuzzy logic to determine whether an alteration in the sensing material 510 is sufficiently close to alterations that are indicative of the odor of an overheating component 320. If the alteration in the sensing material 510 is sufficiently close, the recognition module 412 may determine that the odor within the physical enclosure 202 is indicative of an overheating component 320. The recognition module 412 may compare the alteration with one or more reference alterations that are stored in the reference database 514.

The recognition module 412 may require more than one sample before determining that the odor within the physical enclosure 202 is indicative of an overheating component 320. The recognition module 412 may, in certain embodiments, require that a certain number of samples create an alteration is indicative of an overheating component 320 before the recognition module 412 determines that the odor is indicative of an overheating component 320. The recognition module 412 may require that these samples occur within a particular time frame. For example, the recognition module 412 may require that 60% of the samples cause an alteration indicative of the odor of an overheating component 320 within a thirty-second period. Requiring multiple samples to test positive in this manner may reduce the occurrence of false positive within the system. The number of samples that must test positive in this manner, and the relevant period of time, may vary based on the implementations and the particular needs of the system.

The odor apparatus 160 may also include a reference module 520. The reference module 520 may be responsible for managing the reference database 514. In one embodiment, the reference module 520 may add a particular alteration that occurred in the sensing material 510 to the reference database 514 if the recognition module 412 determines that the odor within the physical enclosure 202 is indicative of an overheating component 320. The addition of this alteration to the reference database 514 may allow the ANN 512 to have an additional alteration from which the ANN 512 can learn, thus using the alteration to improve recognition and detection of odors that are indicative of an overheating component 320.

The reference module 520 may also be configured to receive additional entries to the reference database 514 from one or more other computing devices 100. The odor apparatus 160 may be configured, for example, to communicate over a network that the odor apparatus 160 is communicatively connected to. In such an embodiment, the reference module 520 may receive additional entries to the reference databases 514. The additional entries may be received from other computing devices 100 that have odor apparatus 160 installed and operating.

In one embodiment, the reference module 520 is communicatively connected to a central repository for entries for the reference database 514. For example, the reference module 520 may be configured to retrieve additional entries from a database associated with a remote server. The reference module 520 may poll the database one the remote server at regular intervals in order to find and download additional, new entries for the reference database 514. The reference module 520 may be further configured to upload alterations that occur on the sensing material 510 in the local computing device 100 to the remote server.

In other embodiments, the remote server receives alterations from numerous odor apparatus 160 and maps those alterations to a standard set of data values creating a model from which odors are recognized. The remote server may update the model stored in the reference database 514 at regular intervals. In certain embodiments, the remote server pushes the new model to the reference database 514; in other embodiments, the reference module 520 pulls the new model from the reference database 514.

In this manner, the reference module 520 may allow the reference database 514 to continually receive new information from numerous other odor apparatus 160 that may be installed and in use. The additional to the reference database 514 may allow the recognition module 412 to more accurately recognize alterations in the sensing material 510 that are indicative of an odor of an overheating component 320.

Figure 8:
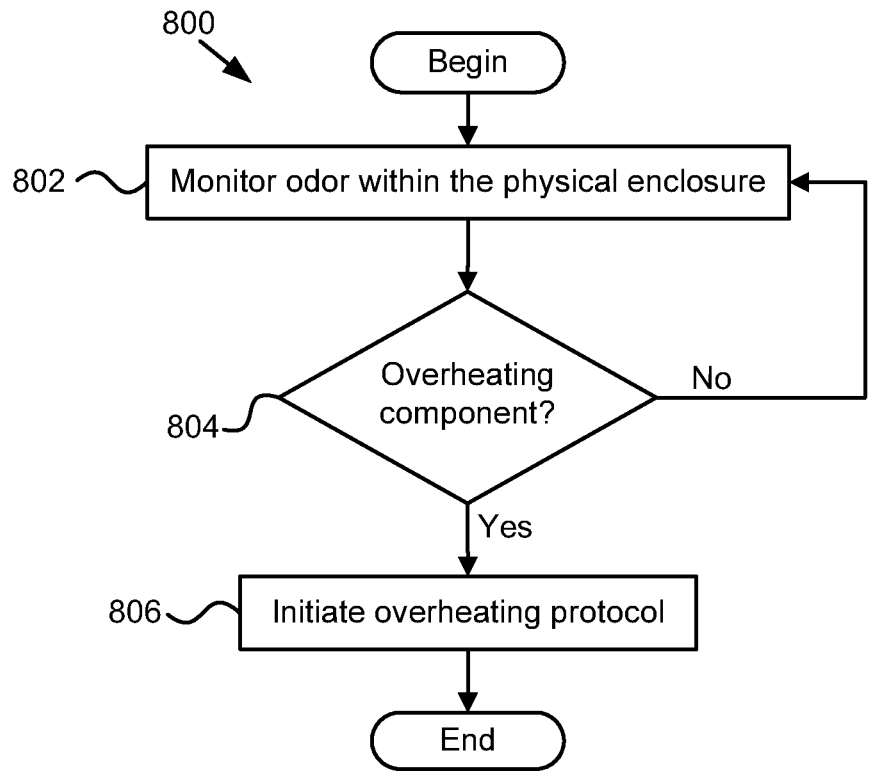
FIG. 8 is a schematic flow chart diagram illustrating one embodiment of a method for determining whether an odor within a physical enclosure of a computing device is indicative of an overheating component.

FIG. 8 shows one embodiment of a method 800 for determining whether a component 320 of a computing device 100 is overheating. The method 800 may begin with monitoring 802 the odor within the physical enclosure 202 of the computing device 100 that comprises one or more components 320. The method 800 may involve, for example, taking samples of the air within the physical enclosure 202 and checking the odor molecules 702 within the sample.

The method 800 may also involve determining 804 whether a component 320 is overheating. The determination may be made by determining, using the odor apparatus 160, that the odor within the physical enclosure 202 is indicative of an overheating component 320 that is overheating within the physical enclosure 202 of the computing device 100. The odor apparatus 160 may include a sensing material 510, as described above, that is reversibly altered by the odor molecules 702 of the odor. For example, the odor molecules 702 may affect the electrical properties of the sensing material 510. An ANN 512 may compare the alteration in the sensing material 510 with a reference database 514 that includes reference alterations that were caused by overheating components 320. The ANN 512 may make the determination based on the comparison of the measured alteration with the reference alterations in the reference database 514.

The method 800 may also involve initiating 806 an overheating protocol. For example, the modules 410-414, 510-516 of the odor apparatus 160 may be used to initiate 806 the overheating protocol. As explained above, the overheating protocol may involve providing appropriate alerts to the user and/or to applications, creating log entries, and taking steps to reduce the possibility of damage to the components 320 in the computing device 100. The specific actions taken as part of the overheating protocol may vary from one implementation to another.

Figure 9:
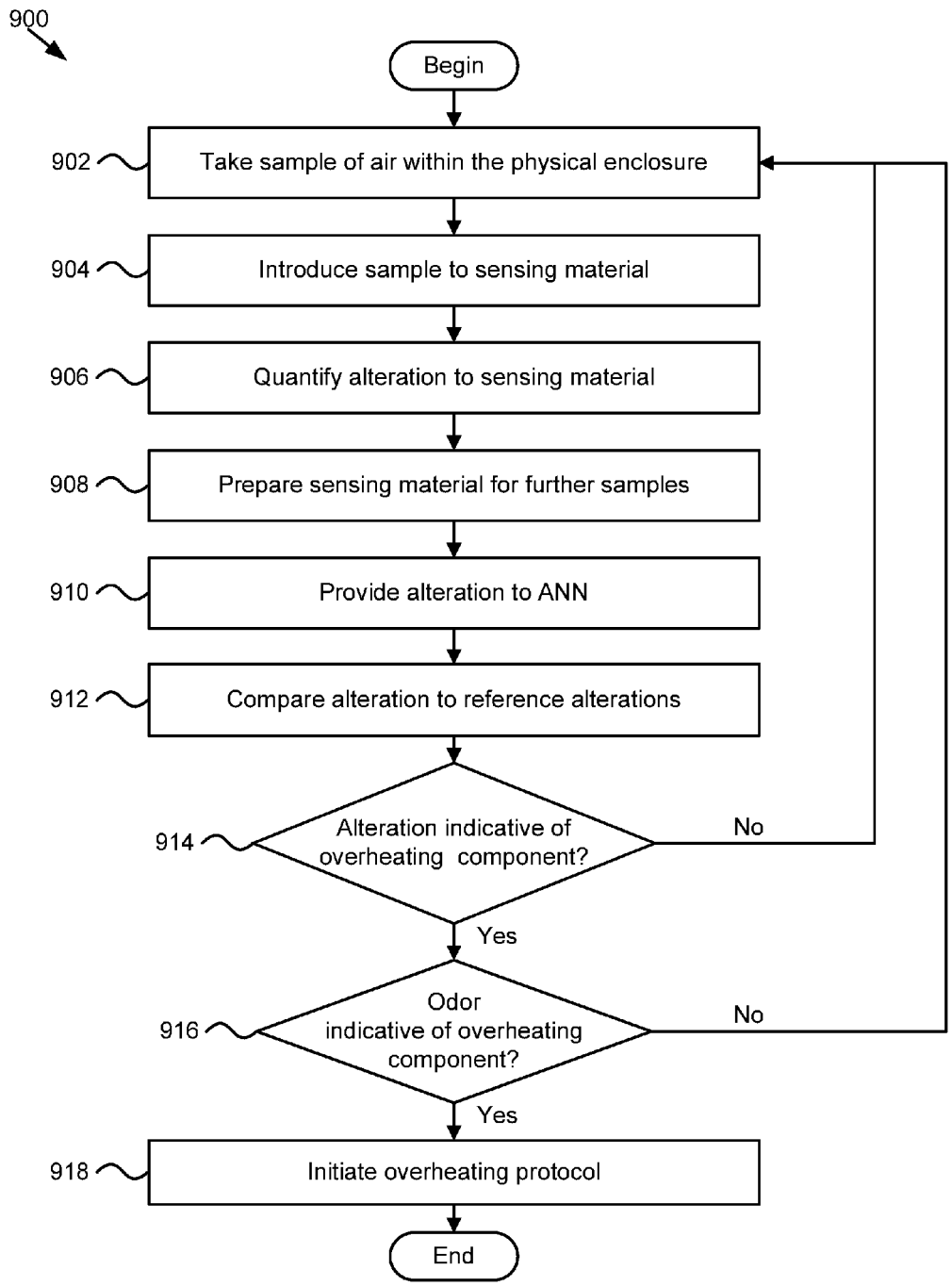
FIG. 9 is a schematic flow chart diagram illustrating a second embodiment of a method for determining whether an odor within a physical enclosure of a computing device is indicative of an overheating component.

FIG. 9 shows a second embodiment of a method 900 for determining whether a component 320 is overheating based on the odor within the physical enclosure 202 that contains the component 320. The method 900 may begin with taking 902 an air sample from within the physical enclosure 202. A sensor module 410 within the physical enclosure 202 may be responsible for taking the sample. The method 900 may also involve introducing 904 the sample to the sensing material 510. The method 900 may further involve quantifying 906 an alteration to the sensing material 510 that results from introduction of the sample. As explained above, the odor molecules 702 may cause a measurable change in the sensing material 510, which change can be measured and quantified in a way that allows for identification and analysis of the odor. The method 900 may further involve preparing 908 the sensing material 510 for further samples. The sensing material 510 may, for example, be cleared of the relevant odor molecules 702 and restored to a baseline value that allows for an additional sample to be introduced and quantified.

In one embodiment, the sensing material 510 is continually in contact with the air within the physical enclosure 202, and is continually quantifying alterations to the sensing material 510. For example, the sensing material 510 may be exposed to within the physical enclosure. In such an embodiment, the method 900 may involve continually quantifying the state of the sensing material 510. The method 900 may also involve occasionally clearing the sensing material 510 and restoring it to a baseline value, thus allowing the sensing material 510 to take new readings of the air in the physical enclosure 202.

The method 900 may also involve providing 910 the alteration, as quantified by the sensor module 410, to an ANN 512. The ANN 512 may compare 912 the alteration to one or more reference alterations that are indicative of an overheating component 320. Based on that comparison, the ANN 512 may determine 914 whether the alteration is indicative of an overheating component 320. If the alteration is not indicative of an overheating component 320, the method 900 may involve repeating the steps of taking 902 a sample, as indicated in FIG. 9.

If the alteration is indicative of an overheating component 320, the method 900 may involve making 916 a further determination as to whether the odor is indicative of an overheating component 320. For example, as explained above, a single sample may be determined to be indicative of an overheating component 320, but the recognition module 412 may require further information before concluding that the odor is indicative of an overheating component 320. The recognition module 412 may require that a plurality of samples yield alterations indicative of an overheating component before concluding that the odor is indicative of an overheating component 320.

The method 900 may further involve initiating 918 the overheating protocol in response to determining that the odor is indicative of an overheating component 320. As noted above, this may involve creating log entries associated with the overheating component 320, alerting the user and/or application programs, and shutting down the computing device 100. In one embodiment, the overheating protocol involves restarting the computing device 100 in a safe boot mode. This may reduce system instability while the problem of the overheating component 320 is diagnosed and addressed.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:
monitoring, using a sensor with a sensing material, an odor within a physical enclosure of a computing device comprising one or more components, the sensor comprising a metal oxide semiconductor field effect transistor ("MOSFET"), the MOSFET acting as a transducer that represents the odor as an electrical signal, wherein the sensing material comprises a gate of the MOSFET and odor molecules interact with gate material of the MOSFET to alter a threshold voltage of the MOSFET;
determining, using an artificial neural network, that the odor within the physical enclosure is indicative of an overheating component that is overheating within the physical enclosure of the computing device, wherein the artificial neural network determines that the odor is indicative of an overheating component by comparing an alteration in the sensing material with a reference database comprising a plurality of reference alterations caused by the overheating component, each reference alteration comprising an electrical signal that corresponds with an odor, wherein determining that the odor within the physical enclosure is indicative of the overheating component comprises determining that the alteration corresponds to one or more of the reference alterations in the reference database; and
initiating an overheating protocol in response to determining that the odor within the physical enclosure is indicative of the overheating component.

2. The method of claim 1, wherein monitoring the odor within the physical enclosure of the computing device comprises collecting one or more samples of odor molecules from within the physical enclosure of the computing device.

3. The method of claim 1, wherein odor molecules of the odor reversibly alter the sensing material for detecting the odor molecules.

4. The method of claim 1, further comprising adding an alteration that occurred in the sensing material to the reference database in response to determining that the odor within the physical enclosure is indicative of the overheating component.

5. The method of claim 4, further comprising receiving one or more additional entries to the reference database from one or more separate computing devices.

6. The method of claim 1, wherein the overheating protocol comprises shutting down the computing device.

7. The method of claim 1, wherein the overheating protocol comprises creating a log entry comprising data generated in connection with the overheating component.

* * * * *